(12) United States Patent
Yin et al.

(10) Patent No.: US 10,822,339 B2
(45) Date of Patent: Nov. 3, 2020

(54) PYRROLOPYRIMIDINE FIVE-MEMBERED AZACYCLIC DERIVATIVE AND APPLICATION THEREOF

(71) Applicants: HANGZHOU HUADONG MEDICINE GROUP BIOPHARMACEUTICAL CO. LTD, Hangzhou, Zhejiang (CN); Jianming Yin, Lexington, MA (US)

(72) Inventors: Jianming Yin, Lexington, MA (US); Yubin Lv, Zhejiang (CN); Bangliang Li, Zhejiang (CN)

(73) Assignees: HANGZHOU HUADONG MEDICINE GROUP BIOPHARMACEUTICAL CO. LTD, Zhejiang (CN); Jianming Yin, Lexington, MA (US)

( * ) Notice: Subject to any disclaimer, the term of this patent is extended or adjusted under 35 U.S.C. 154(b) by 0 days.

(21) Appl. No.: 16/073,027

(22) PCT Filed: Jan. 25, 2017

(86) PCT No.: PCT/CN2017/072535
§ 371 (c)(1),
(2) Date: Jul. 26, 2018

(87) PCT Pub. No.: WO2017/129116
PCT Pub. Date: Aug. 3, 2017

(65) Prior Publication Data
US 2019/0040068 A1   Feb. 7, 2019

(30) Foreign Application Priority Data
Jan. 26, 2016   (CN) .......................... 2016 1 0052851

(51) Int. Cl.
*C07D 487/04* (2006.01)
*A61P 37/06* (2006.01)
*A61P 19/02* (2006.01)
*A61K 31/519* (2006.01)

(52) U.S. Cl.
CPC .......... *C07D 487/04* (2013.01); *A61K 31/519* (2013.01); *A61P 19/02* (2018.01); *A61P 37/06* (2018.01)

(58) Field of Classification Search
CPC ............................ C07D 487/04; A61K 31/519
See application file for complete search history.

(56) References Cited

U.S. PATENT DOCUMENTS

2007/0135461 A1   6/2007   Rodgers et al.
2009/0233903 A1   9/2009   Rodgers et al.
2012/0077798 A1*  3/2012   Rodgers ............... C07D 487/04
                                                        514/210.18
2013/0131039 A1   5/2013   Burgess et al.

FOREIGN PATENT DOCUMENTS

| CN | 101448826 A | 6/2009 |
| EP | 2288610 A1 | 3/2011 |
| JP | 2009519340 A | 5/2009 |
| JP | 2011514909 A | 5/2011 |
| JP | 2013523884 A | 6/2013 |
| WO | 2007070514 A1 | 6/2007 |

OTHER PUBLICATIONS

Notification of Reasons for Refusal for JP Application No. 2018-540042, dated Jun. 11, 2019, 6 pages.
Extended European Search Report for EP Application No. 17743731.6, dated May 21, 2019, 9 pages.
International Search Report issued in PCT/CN2017072535 dated Mar. 21, 2017.
Written Opinion issued in PCT/CN2017072535 dated Mar. 21, 2017.
EPO Office Action for EP Application 17743731.6 dated May 19, 2020; 5 pp.

* cited by examiner

*Primary Examiner* — Susanna Moore
(74) *Attorney, Agent, or Firm* — Armstrong Teasdale LLP

(57) ABSTRACT

The present invention relates to a pyrrolopyrimidine five-membered azacyclic derivative as a novel JAK kinase inhibitor, and use thereof in a preparation of a pharmaceutical product for preventing and/or treating an indication related to a JAK kinase function. The pyrrolopyrimidine five-membered azacyclic derivative of the invention is an ideal JAK kinase inhibitor with a high potency, and can be used to treat or prevent diseases such as rheumatoid arthritis, polycythemia vera, psoriasis, primary thrombocytosis, myelofibrosis, and the like. The pyrrolopyrimidine five-membered azacyclic derivative has the general formula of formula I

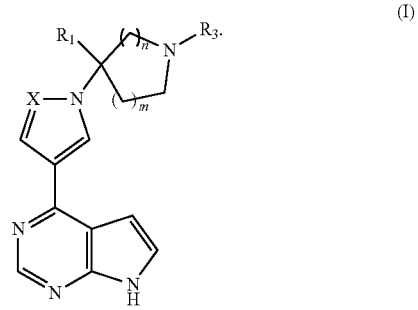

13 Claims, No Drawings

PYRROLOPYRIMIDINE FIVE-MEMBERED AZACYCLIC DERIVATIVE AND APPLICATION THEREOF

This application claims priority to International Application PCT/CN2017/072535, filed on Jan. 25, 2017, which claims priority to CN Patent Application No. 201610052851.X, filed on Jan. 26, 2016, the disclosures of which are hereby expressly incorporated by reference in their entireties.

TECHNICAL FIELD

The present invention relates to a pyrrolopyrimidine five-membered azacyclic derivative and use thereof in a preparation of a medicament for preventing and/or treating an indication related to a JAK kinase function, a preparation method thereof and an intermediate thereof.

TECHNICAL BACKGROUND

JAK kinase (Janus kinase) is an intracellular non-receptor tyrosine kinase that can mediate cytokines and has certain regulatory effect in cell proliferation and function involving immune response. The JAK kinase family has four members, namely JAK kinase 1 (JAK1), JAK kinase 2 (JAK2), JAK kinase 3 (JAK3), and tyrosine kinase 2 (TYK2). In general, cytokines activate JAK kinases by binding to cytokine receptors. After JAK activation, STATs (DNA binding protein) are activated and enter into the nucleus to regulate gene expression. The main signal transduction pathways mediated by the JAKs-STATs family as the cytokine receptors, which may interact with other signal transduction pathways, participate in the development, differentiation, maturation, apoptosis, and functional expression processes of various immune and hematopoietic cells. It plays an extremely important role in regulating organisms' immune and inflammatory response.

Abnormal activation of JAKs-STATs pathway is closely related to many diseases. Thus, JAK kinase inhibitors can be used for the treatment of diseases such as rheumatoid arthritis, polycythemia vera, psoriasis, primary thrombocytosis, and myelofibrosis.

In the development of JAK kinase inhibitors for immune and inflammation-related indications, the first thing to be considered is the inhibitory activity of drugs on JAK2, meanwhile, the selectivity of the drugs to the other three kinases needs to be considered. If the selectivity is not high, serious toxic side effects can easily occur and toxic side effects are mainly reflected in the inhibition of normal human immune function, resulting in a high infection rate. Tofacitinib, the first commercially available JAK kinase inhibitor product, although it has a strong inhibitory activity against JAK2, it has high toxic side effect due to its low selectivity to the other three kinases. In its drug label, it is clearly indicated that the use of Xeljanz (trade name of the Tofacitinib) is associated with increased risk of serious infections, including opportunistic infections, tuberculosis, cancer, and lymphoma etc.

Therefore, it is a difficulty in the art to develop a JAK kinase inhibitor that is both highly active and safe.

SUMMARY OF THE INVENTION

The technical problem to be solved by the present invention is to provide a novel JAK kinase inhibitor with high activity and safety.

The present invention provides a pyrrolopyrimidine five-membered azacyclic derivative which is an ideal JAK kinase inhibitor.

The present invention also provides the use of a pyrrolopyrimidine five-membered azacyclic derivative, a pharmaceutically acceptable salt and hydrate thereof, or metabolite metabolized in any form in a preparation of a medicament for preventing and/or treating indications related to JAK kinase function.

In order to solve the above technical problems, the present invention adopts the following technical solutions:

A pyrrolopyrimidine five-membered azacyclic derivative, a pharmaceutically acceptable salt and hydrate thereof, or metabolite metabolized in any form, the structural formula of the pyrrolopyrimidine five-membered azacyclic derivative is shown in formula (I):

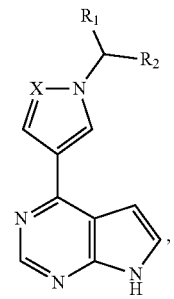

wherein:
X is N or CH;
$R_1$ is $CH_2CN$ or $COCH_2CN$;
$R_2$ is

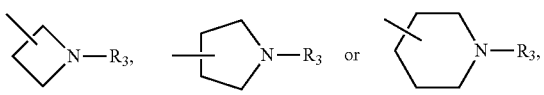

wherein $R_3$ is $SO_2R_4$ or $C(O)R_4$, $R_4$ is a linear or cyclic alkyl group, a linear or branched hydrocarbon chain having at least one double bond, a linear or cyclic alkyl group substituted with fluorine, $NHCH_3$, $N(CH_3)_2$, phenyl, pyridine or pyrimidine.

Preferably, in the pyrrolopyrimidine five-membered azacyclic derivative, the pharmaceutically acceptable salt and hydrate thereof, or metabolite metabolized in any form, non-exchangeable hydrogen is not substituted, partially or completely substituted by deuterium.

Preferably, $R_4$ is a linear or cyclic alkyl group having 1 to 6 carbon atoms or a hydrocarbon group having one double bond and having 2 to 6 carbon atoms. More preferably, $R_4$ is methyl, ethyl, vinyl, or cyclopropyl.

Further, in the formula (I), $R_1$ is $CH_2CN$ and $R_3$ is $SO_2R_4$.

Preferably, in formula (I), $R_3$ is $SO_2CH_2CH_3$.

Preferably, the pyrrolopyrimidine five-membered azacyclic derivative is one of the compounds represented by the following structural formulas or a mixture of more thereof:

Ia 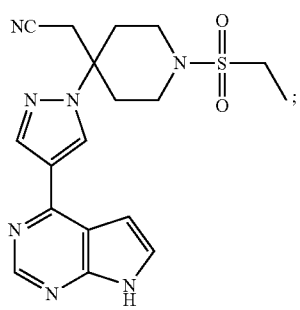
If 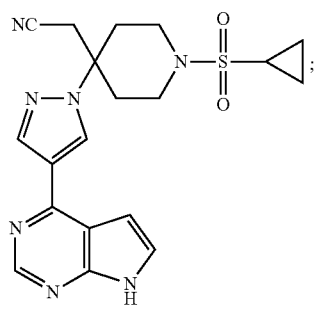
Ib 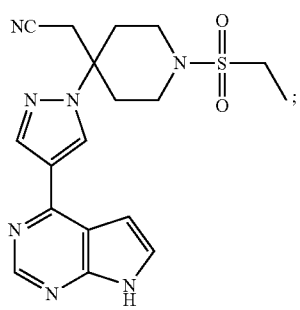
Ig 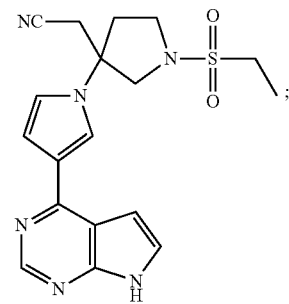
Ic 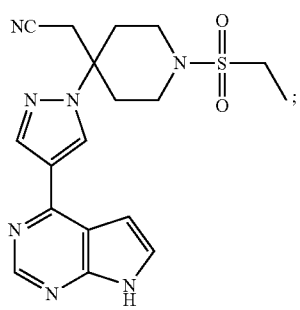
Ih 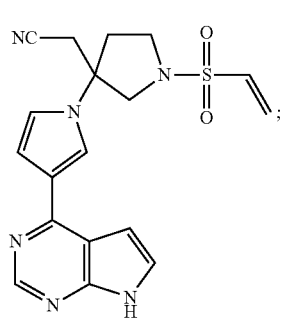
Id 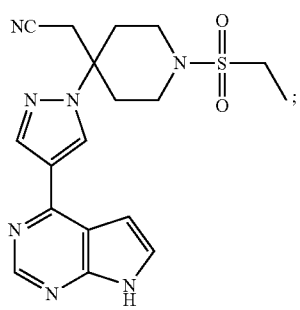
Ii 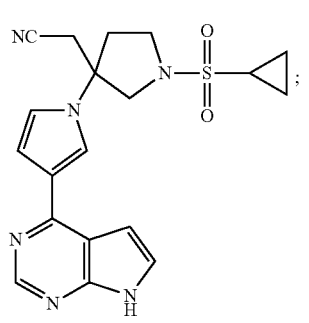
Ie 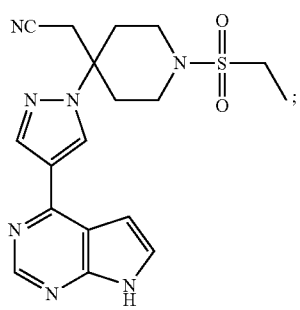
Ij 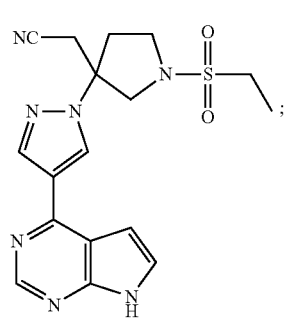

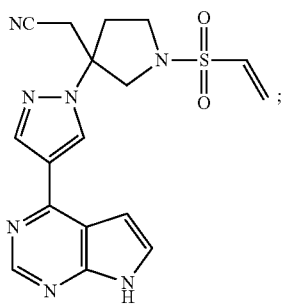

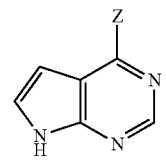

is reacted with a first amino protective reagent PG₁ to obtain

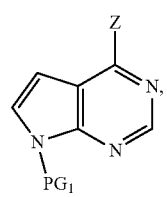

wherein Z is Cl, Br, or I;

(b) The product obtained in step (a) is reacted with

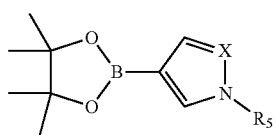

to obtain

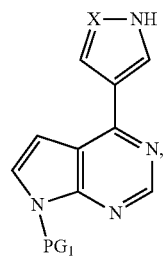

wherein R₅ is an alkoxy group or a silane group which are as amino protecting groups; when R₅ is an alkoxy group, first of all, the product obtained in step (a) and

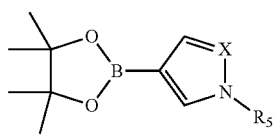

are placed in a mixed solvent of alcohol and water, and the reaction is carried out under a catalyst and a basic condition, so that the group According to the present invention, the compound of the pyrrolopyrimidine five-membered azacyclic derivative includes not only a single compound form, a mixture form comprising the various compounds with the structures satisfying the requirements of the general formula (I), but also different isomeric forms of the same compound such as racemates, enantiomers, diastereomers and the like. The pharmaceutically acceptable salts include, but are not limited to, hydrochlorides, phosphates, sulfates, acetates, maleates, methanesulfonates, benzenesulfonates, benzoates, methylbenzenesulfonates, succinates, fumarates, tartrates, gallates, citrates, etc. The term "prodrug of a compound having the general formula (I)" refers to a substance which, when administered by an appropriate method, can be metabolized or chemically reacted in the body of subjects to transform into at least one compound of structural formula (I) or a salt thereof.

The present invention also provides a pharmaceutical composition comprising said pyrrolopyrimidine five-membered azacyclic derivative or the pharmaceutically acceptable salt thereof, and a pharmaceutically acceptable carrier.

The preparation of the pyrrolopyrimidine five-membered azacyclic derivative of the present invention can be achieved by synthetic routes similar to those well-known in the chemical arts, and in particular according to the description contained herein. Reagents are generally obtained from commercial sources or are readily prepared using methods well-known to those skilled in the art.

Another object of the present invention is to provide a method for preparing the above pyrrolopyrimidine five-membered azacyclic derivative, which comprises the following steps:

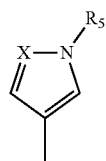

replaces Z and then $R_5$ is removed under an acidic reaction condition;

(c)

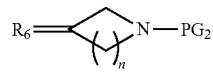

is used, wherein $PG_2$ is a second aminoprotecting group, and the product obtained in step (b) is subjected to an addition reaction with

followed by deprotection of the second aminoprotecting group $PG_2$ under an acidic condition to obtain

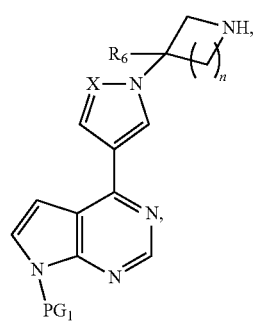

wherein $R_6$ is CHCN or CH(CO)CN, $R_1$ is defined as before, and n is an integer from 1 to 3;

(d) a substitution reaction is carried out in a polar solvent between the product obtained in step (c) and $R_3$—Cl

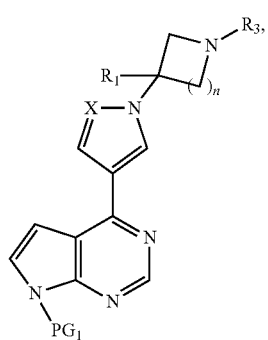

to obtain then the first amino protecting group $PG_1$ is removed to obtain

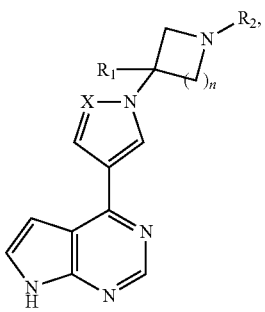

i.e. a compound of formula (I).

An exemplary specific synthetic route is as follows:

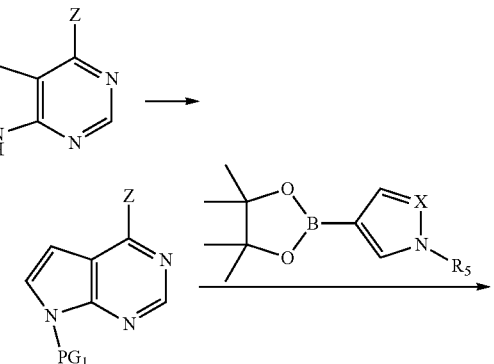

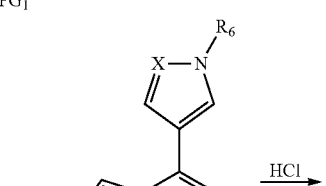

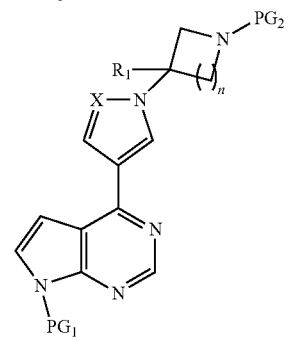

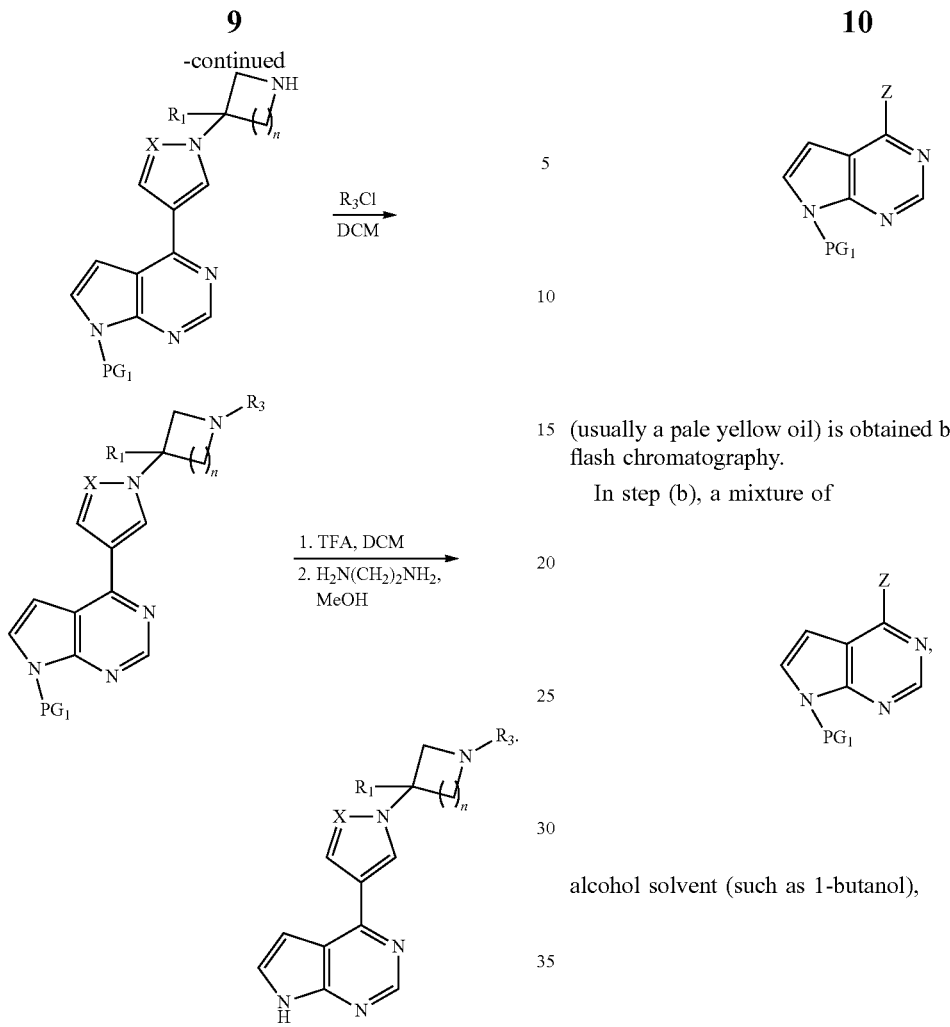

(usually a pale yellow oil) is obtained by the purification by flash chromatography.

In step (b), a mixture of

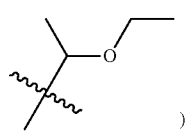

alcohol solvent (such as 1-butanol),

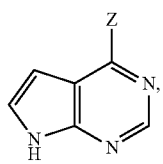

Those skilled in the art can obtain the reaction conditions of the above preparation methods of the pyrrolopyrimidine five-membered azacyclic derivative according to the prior art; the methods can also be carried out according to the following preferred preparation and purification schemes to increase the yield and purity of the product and reduce the cost.

In step (a), the first amino protection reagent can be 2-(trimethylsilyl)ethoxymethyl chloride (SEMCl, $PG_1$ is SEM here), and at this time, the suspension of NaH and DMF can be slowly added in a DMF solution of the mixture is stirred below 5° C. for 0.5 to 5 hours; then SEMCl is slowly added and stirred overnight at room temperature, the reaction is quenched by adding water, and the reaction product is extracted with ethyl acetate, filtered and concentrated under reduced pressure;

water and carbonate (such as potassium carbonate) is stirred at 60~100° C., followed by the addition of tetrakis(triphenylphosphine)palladium (0), the mixture is stirred at 60~100° C. overnight and then cooled to room temperature, the reaction mixture is filtered through a diatomite bed, extracted and concentrated under reduced pressure, and purified by silica gel column; It should be noted that: $R_5$ may be an alkoxy group as amino protecting group that cannot be hydrolyzed (such as or a hydrolysable silane group as amino protecting group (such as

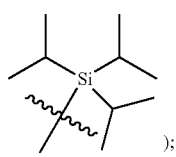 [SMILES: *[Si](C(C)C)(C(C)C)C(C)C]

when $R_5$ is a silane group,

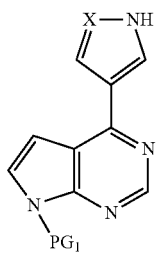

is obtained directly; when $R_5$ is an alkoxy group, the product obtained by silica gel column purification further needs to be stirred overnight under an acidic condition (the product is dissolved in THF and HCl aqueous solution is added), concentrated under reduced pressure, then extracted with ethyl acetate, dried, filtered, concentrated and purified by silica gel column to obtain

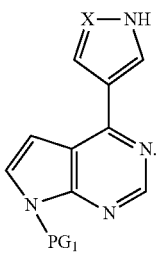

In step (c), the product obtained in step (b),

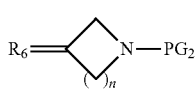

(n is an integer from 1 to 3), acetonitrile and DBU are mixed to form a mixture, and the mixture is stirred at 50-90° C. for 1 to 5 hours, then the reaction mixture is concentrated under reduced pressure and purified by silica gel column. In step (d), a mixture of the product obtained in step (c), DCM, triethylamine and ethyl sulfonyl chloride is stirred at room temperature overnight. The reaction mixture is then concentrated under reduced pressure and purified by flash chromatography to obtain

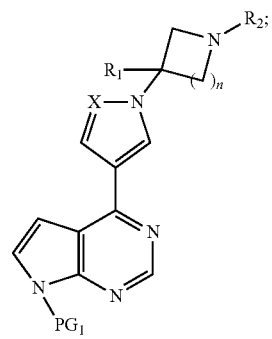

then its DCM solution is added to TFA below 5° C., the mixture is stirred at room temperature for 0.5 to 5 hours, concentrated under reduced pressure; methanol and ethylenediamine are added to the residue, the mixture is stirred at room temperature for 1 to 5 hours, the solvent is removed, and the solute is purified by HPLC.

Still another object of the present invention is to provide an intermediate of the above pyrrolopyrimidine five-membered azacyclic derivative, the intermediate has a structural formula as shown in formula (II):

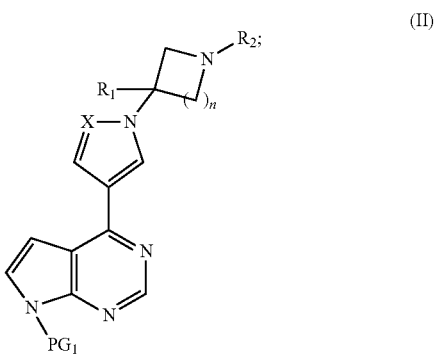

wherein: $PG_1$ is a first amino protecting group, $R_7$ is a second amino protecting group $PG_2$, H or $R_3$. The first amino protecting group $PG_1$ and the second amino protecting group $PG_2$ can be those conventionally used, for example, the first amino protecting group $PG_1$ is 2-(trimethylsilyl)ethoxymethyl (SEM), and the second amino protecting group $PG_2$ is tert-butyloxycarbonyl (Boc).

Further, the general structure of the intermediate of pyrrolopyrimidine five-membered azacyclic derivative is:

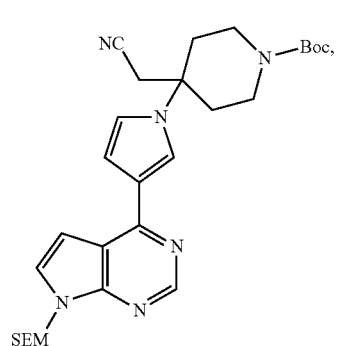

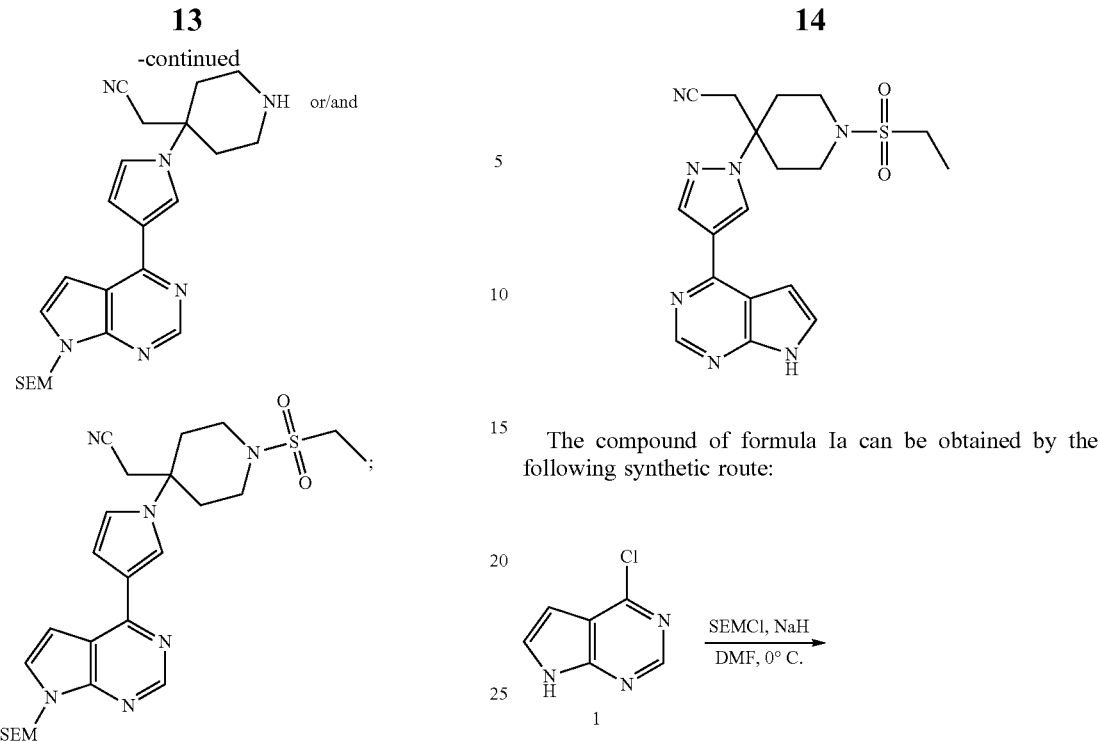

they are all intermediates of the pyrrolopyrimidine five-membered azacyclic derivative, which are in the different steps of the preparation method thereof.

Another technical solution utilized by the present invention: the use of the pyrrolopyrimidine five-membered azacyclic derivative, the pharmaceutically acceptable salt and hydrate thereof, or metabolite metabolized in any form in a preparation of a medicament for preventing and/or treating indications related to JAK kinase function.

The indications related to JAK kinase function include, but are not limited to, rheumatoid arthritis, polycythemia vera, psoriasis, primary thrombocytosis, myelofibrosis, and the like.

Due to the implementation of the above technical solutions, the present invention has the following advantages over the prior art:

The compounds provided by the present invention, the pyrrolopyrimidine five-membered azacyclic derivative, are novel JAK kinase inhibitors with high activity and selectivity, and have certain curative effect in terms of immune and inflammatory response through inhibiting JAK kinase, while having less toxic side effects, and is highly safe. Thus, the compounds of the present invention can be used to prepare a medicament for treating or preventing various indications related to the JAK kinase function.

EMBODIMENTS

The present invention will be further described in detail with reference to specific embodiments, but the present invention is not limited to the following embodiments.

Example 1

This example provides a pyrrolopyrimidine five-membered azacyclic derivative (the compound of formula Ia), whose chemical structure is as follows:

The compound of formula Ia can be obtained by the following synthetic route:

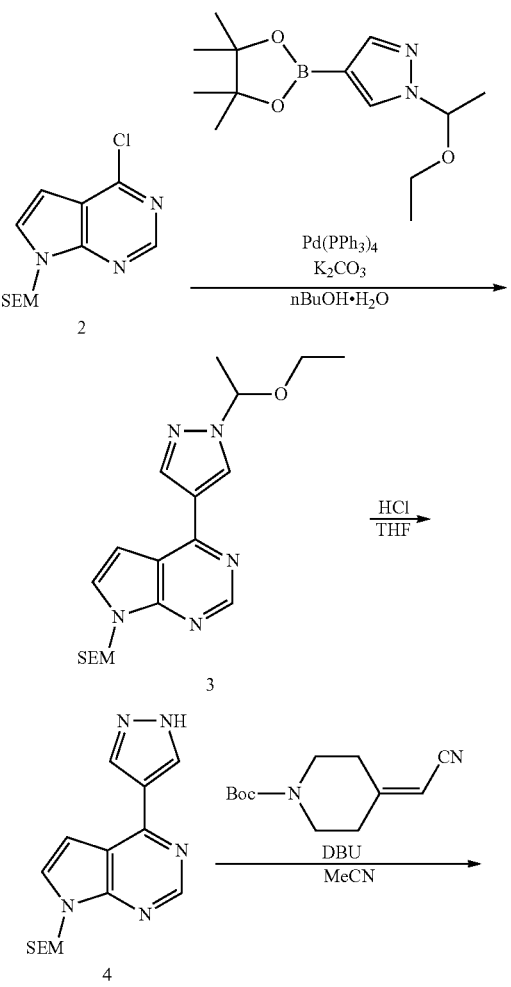

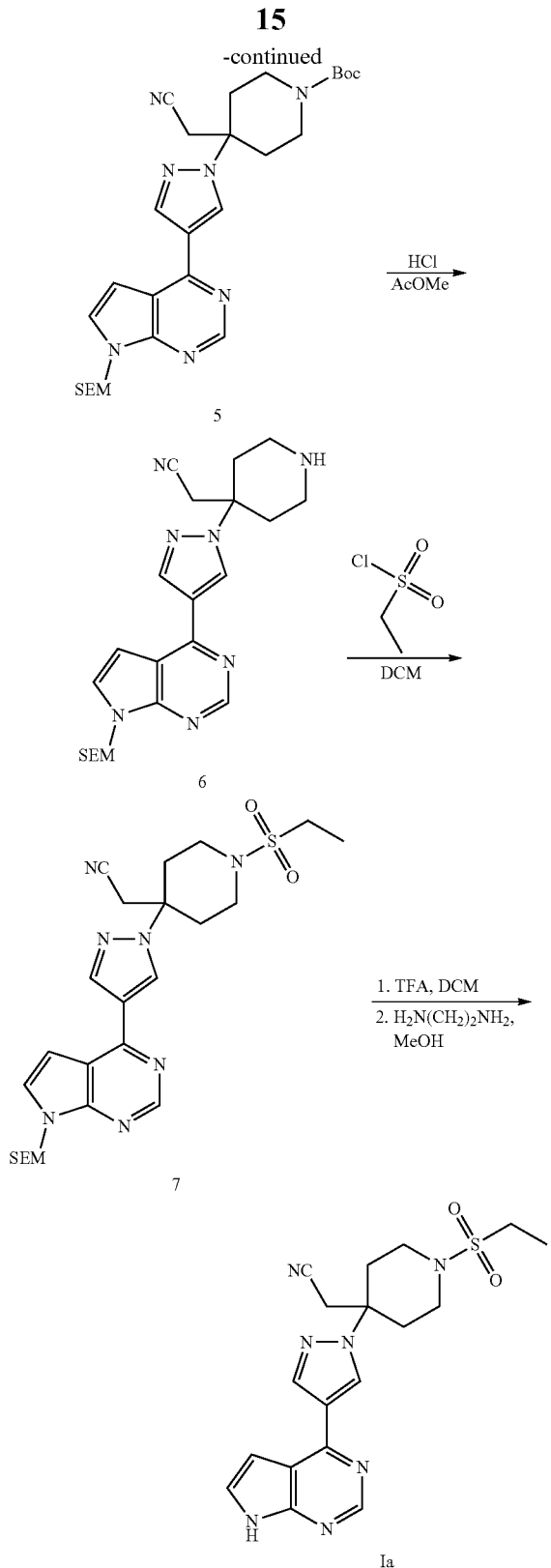

light brown turbid mixture. Then 2-(trimethylsilyl)ethoxymethyl chloride (SEMCl) (12.7 g, 0.08 mol) was slowly added to the turbid mixture, the newly obtained mixture was stirred overnight at room temperature, the reaction was quenched with water and extracted with ethyl acetate, filtered and concentrated under reduced pressure. Intermediate 2 (15 g, 81%) was obtained by flash chromatography purification as a pale yellow oil; MS (m/s): 284 [M+H]$^+$; $^1$H-NMR (400 MHz, DMSO-D6): δ 0.00 (s, 9H), 0.95 (t, J=11.6 Hz, 2H), 3.68 (t, J=10 Hz, 2H), 5.79 (s, 2H), 6.79 (s, 1H), 7.98 (s, 1H), 8.78 (s, 1H).

(2) Preparation of intermediate 3: a mixture of intermediate 2 (8 g, 283 mol), 1-butanol (30 mL), 1-(1-ethoxyethyl)-4-(4,4,5,5-tetramethyl-1,3,2-dioxaborolan-2-yl)-1H-pyrazole (9 g, 0.034 mol), water (30 mL) and potassium carbonate (9.9 g, 0.071 mol) was stirred at 100° C. Tetrakis(triphenylphosphine)palladium (0) (3.3 g, 2.8 mmol) was then added to the solution, the mixture was stirred at 100° C. overnight. After cooled to room temperature, the mixture was filtered through a diatomite bed, extracted and concentrated under reduced pressure, and purified by silica gel column to obtain intermediate 3 (8.5 g, 78%) as a yellow oil; $^1$H-NMR (400 MHz, DMSO-d6): δ 0.00 (s, 9H), 0.95 (t, J=8 Hz, 2H), 1.17-1.22 (m, 3H), 1.84 (d, J=6 Hz, 3H), 3.43-3.40 (m, 1H), 3.63-3.67 (m, 4H), 5.78 (s, 2H), 7.28 (d, J=3.6 Hz, 1H), 7.88 (d, J=3.6 Hz, 1H), 8.54 (s, 1H), 8.92 (s, 1H), 8.96 (s, 1H).

(3) Preparation of intermediate 4: 1.5 N HCl aqueous solution (20 mL) was added to a solution of intermediate 3 (8.5 g, 0.022 mol) and THF (80 mL), and the mixture was stirred at room temperature overnight. The reaction mixture was then concentrated under reduced pressure, extracted with ethyl acetate, dried, filtered and concentrated, purified by silica gel column to obtain intermediate 4 (4.8 g, 69%) as a white solid; MS (m/s): 316 [M+H]$^+$; $^1$H-NMR (400 MHz, DMSO-d$_6$): δ 0.00 (s, 9H), 0.91 (t, J=8 Hz, 2H), 3.65 (t, J=8 Hz, 2H), 5.73 (s, 2H), 7.18 (s, 1H), 7.83 (s, 1H), 8.44 (s, 1H), 8.77 (s, 1H), 8.84 (s, 1H), 13.50 (s, 1H).

(4) Preparation of intermediate 5: a mixture of intermediate 4 (4.5 g, 0.143 mol), acetonitrile (50 mL), tert-butyl 4-(cyanomethylene)piperidine-1-carboxylate (4.67 g, 0.214 mol) and DBU (2.2 g, 0.0143 mol) was stirred at 70° C. for 4 hours. The reaction mixture was then concentrated under reduced pressure. Solid intermediate 5 (3.5 g, 45%) was obtained by silica gel column purification; $^1$H-NMR (400 MHz, DMSO-d6): δ 0.00 (s, 9H), 0.92 (t, J=7.2 Hz, 2H), 1.5 (s, 9H), 2.12 (t, J=12 Hz, 2H), 2.77 (d, J=14.4 Hz, 2H), 3.10 (s, 2H), 3.60 (s, 2H), 3.64 (t, J=8 Hz, 2H), 3.89 (d, J=32 Hz, 2H), 5.74 (s, 2H), 7.30 (d, J=3.6 Hz, 1H), 7.89 (d, J=3.6 Hz, 1H), 8.55 (s, 1H), 8.62 (s, 1H), 8.96 (s, 1H).

(5) Preparation of intermediate 6: intermediate 5 (3.5 g, 6.5 mmol) was added to 20 mL of 4N HCl methyl acetate solution, the mixture was stirred at room temperature overnight. The reaction mixture was then concentrated under reduced pressure. White solid intermediate 6 (1.4 g, 50%) was obtained by silica gel column purification; MS (m/s): 438 [M+H]$^+$.

(6) Preparation of intermediate 7: a mixture of intermediate 6 (1.4 g, 3.2 mmol), DCM (20 mL), triethylamine (0.5 g, 4.95 mmol) and ethyl sulfonyl chloride (0.5 g, 3.89 mmol) was stirred at room temperature overnight. The reaction mixture was then concentrated under reduced pressure, purified by flash chromatography to obtain intermediate 7 (0.5 g, 30%) as a white solid; MS (m/s): 530 [M+H]$^+$; $^1$H-NMR (400 MHz, DMSO-d6): δ 0.00 (s, 9H), 0.92 (m, J=8 Hz, 2H), 1.25 (t, J=7.2 Hz, 3H), 2.17-2.23 (m, 2H), 2.89-2.92 (m, 2H), 3.00-3.12 (m, 4H), 3.38 (s, 1H), 3.43 (s, The method for preparing the compound of formula Ia specifically includes the following steps:

(1) Preparation of intermediate 2: a solution of 1 (10 g, 0.066 mol) in DMF (40 mL) was slowly added to a suspension of NaH (3 g, 0.13 mol) and DMF (60 mL) at 0° C. The reaction mixture was stirred at 0° C. for 2 hours to obtain a 1H), 3.60-3.64 (m, 4H), 5.74 (s, 2H), 7.30 (d, J=3.6 Hz, 1H), 7.90 (d, J=3.6 Hz, 1H), 8.56 (s, 1H), 8.87 (s, 1H), 8.94 (s, 1H).

(7) Preparation of the compound of formula Ia: a solution of intermediate 7 (0.1 g, 0.189 mmol) and DCM (5 mL) was added to TFA (5 mL) at 0° C. The reaction mixture was stirred at room temperature for 1 h. The mixture was then concentrated under reduced pressure, methanol (5 mL) and ethylene diamine (1 mL) were added to the residue, and the mixture was stirred at room temperature for 2 hours. The solvent was then removed, the solute was purified by HPLC to obtain Ia compound (25 mg, 33%) as a white solid.

The obtained target product Ia was subjected to H-nuclear magnetic resonance $^1$H-NMR (400 MHz, MeOD) and mass spectrometry tests. The results are as follows:

Absorption peaks in $^1$H-NMR spectrum: δ=8.81 (s, 1H) 8.70 (s, 1H) 8.45 (s, 1H) 7.61 (d, 1H) 7.09 (d, 1H) 6.06 (s, 1H) 3.56 (d, 2H) 3.29 (s, 2H) 3.03 (m, 2H) 2.93 (t, 2H) 2.82 (t, 2H) 2.10 (m, 2H) 1.15 (t, 3H).

m/z [MH]$^+$: 400.2. It was obtained by calculation that the product has the formula $C_{18}H_{21}N_7O_2S$, with an exact molecular weight (exact mass) of 399.15.

Example 2

The compound of formula Ib, whose chemical structure is as follows:

The compounds of formula Ib can be obtained by the following synthetic route:

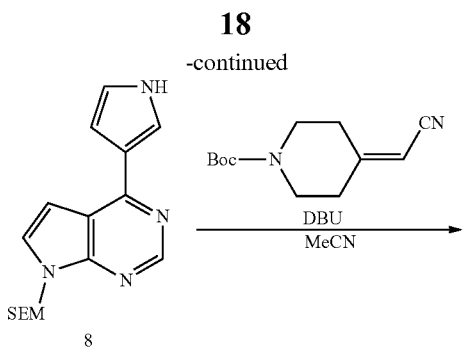

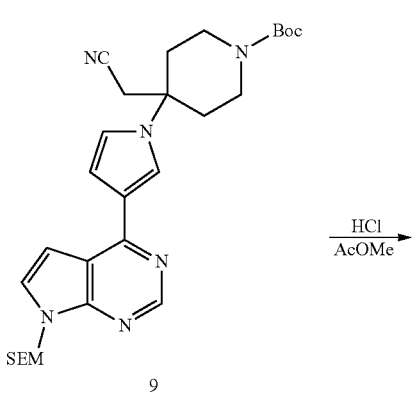

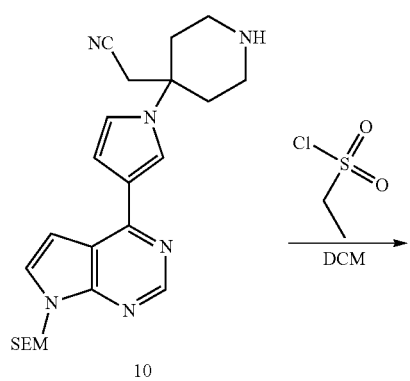

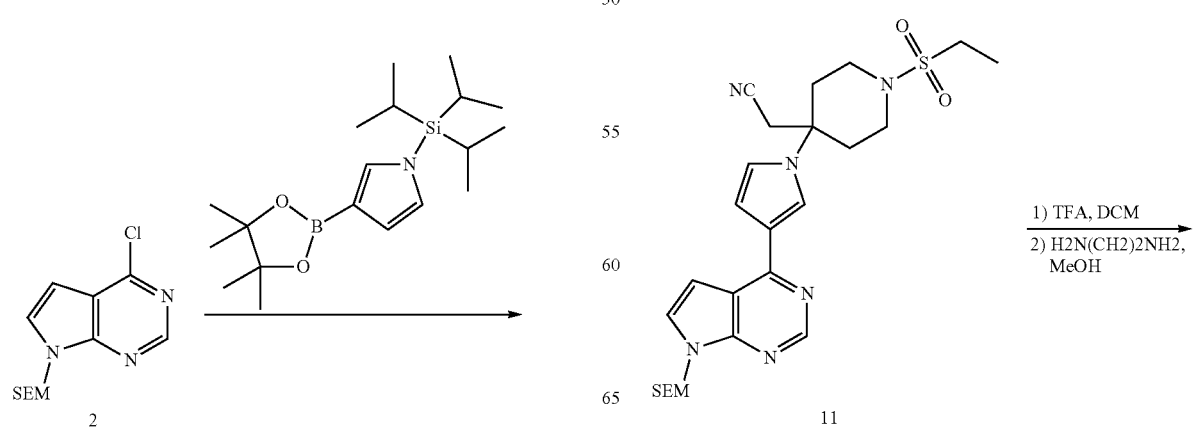

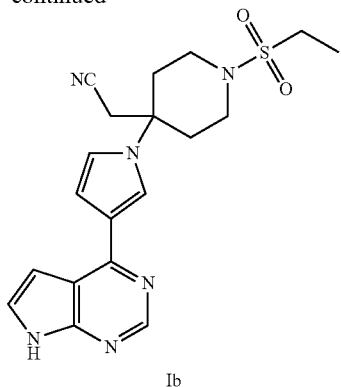

Ib

The method for preparing the compound of formula Ib specifically includes the following steps:

(1) Preparation of intermediate 8: a mixture of intermediate 2 (3 g, 10.6 mmol), 1-butanol (30 mL), 3-(4,4,5,5-tetramethyl-1,3,2-dioxaborolan-2-yl)-1-(triisopropylsilyl)-1H-pyrrole (4.5 g, 12.7 mmol), water (30 mL) and potassium carbonate (3.7 g, 26.5 mmol) was stirred at 100° C. Tetrakis(triphenylphosphine)palladium (0) (0.7 g, 0.53 mmol) was then added to the solution, and the mixture was stirred at 100° C. overnight. After cooled to room temperature, the mixture was filtered through a diatomite bed, extracted and concentrated under reduced pressure, and purified by silica gel column to obtain intermediate 8 (2 g, 60%) as a yellow oil; MS (m/s): 315 [M+H]$^+$.

(2) Preparation of intermediate 9: a mixture of intermediate 8 (2 g, 6.4 mmol), acetonitrile (60 mL), tert-butyl 4-(cyanomethylene)piperidine-1-carboxylate (2.1 g, 9.5 mmol) and DBU (1.5 g, 9.9 mmol) was stirred at 70° C. for 4 hours. The reaction mixture was then concentrated under reduced pressure and purified by silica gel column to obtain solid intermediate 9 (1 g, 30%); MS (m/s): 537 [M+H]$^+$; $^1$H-NMR (400 MHz, CDCl$_3$): δ 0.00 (s, 9H), 0.95-1.00 (m 2H), 1.51 (s, 9H), 2.13-2.17 (m, 2H), 2.53-2.60 (m, 2H), 2.84 (s, 2H), 3.20 (brs, 2H), 3.60 (t, J=8.4 Hz, 2H), 3.99 (brs, 2H), 5.72 (s, 2H), 6.91 (d, J=3.6 Hz, 1H), 7.04-7.09 (m, 2H), 7.40 (s, 1H), 7.82 (s, 1H), 8.87 (s, 1H).

(3) Preparation of intermediate 10: intermediate 9 (1 g, 1.86 mmol) was added to 10 mL of 4N HCl methyl acetate solution and stirred at room temperature overnight. The reaction mixture was then concentrated under reduced pressure. White solid intermediate 10 (0.7 g, 86%) was obtained by silica gel column purification; MS (m/s): 437 [M+H]$^+$.

(4) Preparation of intermediate 11: a mixture of intermediate 10 (0.7 g, 1.4 mmol), DCM (15 mL), triethylamine (0.25 g, 2.5 mmol) and ethyl sulfonyl chloride (0.25 g, 1.9 mmol) was stirred at room temperature overnight. The reaction mixture was then concentrated under reduced pressure and purified by flash chromatography to obtain intermediate 11 (0.25 g, 30%) as a white solid; MS (m/s): 529 [M+H]$^+$.

(5) Preparation of compound of formula Ib: a solution of intermediate 11 (0.25 g, 0.48 mmol) and DCM (10 mL) was added to TFA (10 mL) at 0° C. The reaction mixture was stirred at room temperature for 1 hour. The mixture was then concentrated under reduced pressure, methanol (10 mL) and ethylenediamine (2 mL) were added to the residue, and the mixture was stirred at room temperature for 2 hours. The solvent was then removed, the solute was purified by HPLC to obtain Ib compound (22 mg, 12%) as a white solid.

The obtained target product Ib was subjected to H-nuclear magnetic resonance $^1$H-NMR (400 MHz, MeOD) and mass spectrometry tests. The results were as follows: absorption peaks in $^1$H-NMR spectrum: δ=11.16 (s, 1H) 8.84 (s, 1H) 7.78 (s, 1H) 7.27 (d, 1H) 7.07 (t, 1H) 6.99 (t, 1H) 6.85 (d, 1H) 3.80 (d, 2H) 3.03 (t, 2H) 2.91 (t, 2H) 2.78 (s, 2H) 2.70 (d, 2H) 2.18 (t, 2H) 1.29 (t, 3H). m/z [MH]$^+$:399.2. It was obtained by calculation that the product has the formula $C_{19}H_{22}N_6O_2S$, with an exact molecular weight (extract mass) of 398.15.

Efficacy Etc. Test

I. Test of the Enzyme Activity of the Compounds:

1. Experiment Method

The semi-inhibitory concentration IC$_{50}$ of the compounds (the concentration of the compounds required to inhibit enzyme activity to 50%) is determined by the immobilized enzyme mixed with a specific substrate and different concentrations of the test compounds. The determination method used was a Caliper Mobility Shift Assay. The kinases determined were JAK1, JAK2, JAK3 and TYK2. The standard reference compound used was staurosporine.

2. Experiment Results

It is summarized in table 1 the results of the enzyme activity inhibition experiments of the compounds. The results showed that the compounds of the present invention (Ia and Ib) had very strong inhibitory effects on JAK2 kinase; at the same time, the results showed that the compounds of the present invention (Ia and Ib) had good selective inhibitory activities. The selective inhibition has important therapeutic significance for the treatment of the diseases such as rheumatoid arthritis, polycythemia vera, psoriasis, primary thrombocytosis, and myelofibrosis and so on.

TABLE 1

Results of the enzyme activity inhibition experiments of the compounds

| | Kinase inhibitory activity (IC$_{50}$, nM) | |
| --- | --- | --- |
| Kinase | Compound of formula Ia | Compound of formula Ib |
| JAK1 | 21 | 31 |
| JAK2 | 0.2 | 0.4 |
| JAK3 | 27 | — |
| TYK2 | 7.3 | — |

II. Electrophysiological Assessment of the Compounds In Vitro:

1. Experiment Method

Potassium channel current blocking percentage of whole cell hERG by the compounds of the present invention is studied using HEK293 cells expressing hERG stably and automatic patch clamp system detection method, the dose-effect relationship curve was obtained. The positive drug is Cisapride.

2. Experiment Results

The IC$_{50}$ values of the compounds of the present invention (Ia and Ib) obtained by the test dose-effect relationship curve were all greater than 30 μM, indicating that the compounds of the present invention have very low probabilities of cardiotoxicity of the drug brought by prolonged QT interval.

III. Rat Adjuvant-Induced Arthritis Efficacy Model Test:

1. Experiment Method (1) Modeling: *Mycobacterium tuberculosis* H37Ra was dissolved in paraffin oil to prepare CFA, intradermal injection was carried out in the base of tail of rat with a dose of 100 μL, the disease occurred in rat on the 14th day, and the clinical score of the simultaneous occurrence of the disease was ≥3.

(2) Treatment: the rats were then randomly assigned groups and orally administered with the compounds of the present invention (Ia and Ib, at doses of 0.5 mg/kg, 1.0 mg/kg, 1.5 mg/kg, 10 mg/kg, and 15 mg/kg, respectively). The entire dosing period was 14 days and clinical scores and paw volume measurement were performed on Mondays and Thursdays, the data were recorded.

2. Experiment Results

The experimental results showed that the clinical score, joint swelling and paw volume of the model groups were all higher than those of the normal group. From the results of the HE section, the model groups had infiltration of inflammatory cells and proliferation of connective tissue. X-ray also showed that the model group had obvious hyperostosis, the spaces of articular surfaces were not clear, and there was a sense of burrs. In summary, this modeling was successful.

The compounds of the present invention can effectively inhibit rat lesions in clinical scores, paw volume, HE sections and X-ray. The animal clinical scores and paw volumes of compounds Ia and Ib in the dose groups of 10 mg/kg and 15 mg/kg are almost close to the normal group, HE sections and X-ray also confirmed that the efficacy was significant, the state of the rats were significantly improved. The inhibition rates (relative to the vehicle group, clinical score) of the compound Ia at the doses of 0.5 mg/kg, 1.0 mg/kg, 1.5 mg/kg, 10 mg/kg, and 15 mg/kg were 16%, 28%, 50%, 100% and 100% respectively. The treatment groups of the compounds Ia and Ib had greater increases in animal body weight than that of the vehicle group.

IV. Pharmacokinetic Experiments

1. Experiment Method:

Experimental animals: Beagles, male and female; body weight: 7-9 kg;

Preparation of test samples: the compound (Ia) of the present invention was formulated into 2.5 mg/mL (for intravenous administration) and 2.0 mg/mL (for oral administration) for use. Routes of administration: oral/intravenous injection. Dosing capacity and frequency: 2 mL/kg (intravenous injection) or 5 mL/kg (oral), single administration.

Sample collection: blood was collected at the following time points: post-dose at 5 min, 15 min, 30 min, 1 hr, 2 hrs, 4 hrs, 8 hrs, and 24 hrs.

2. Sample Analysis and Results

Sample analysis: The collected samples were tested using the LC-MS/MS method. The instrument model is API4000.

Pharmacokinetic data analysis: WinNolin was used to fit and calculate the obtained plasma concentration data according to the non-compartmental model method. Some results are summarized in table 2.

TABLE 2

Pharmacokinetic parameters of the target compound calculated according to the non-compartmental model method

| Dose (mg/kg) | Routes of administration | Pharmacokinetic parameters (unit) | Compound of formula Ia |
|---|---|---|---|
| 5 | Intravenous injection N = 3 | CL (L/hr/kg) | 0.45 |
| | | Vss (L/kg) | 1.85 |
| | | Terminal $t_{1/2}$ (hr) | 4.78 |
| | | $AUC_{last}$(hr*ng/mL) | 10932 |
| | | $MRT_{INF}$(hr) | 4.16 |
| 10 | Oral N = 3 | $T_{max}$ (hr) | 0.25 |
| | | $C_{max}$ (ng/mL) | 2502 |
| | | Terminal $t_{1/2}$ (hr) | 5.79 |
| | | $AUC_{last}$(hr*ng/mL) | 10619 |
| | | F (%) | 49.4 |

The experiment results show that the compounds of the present invention have good pharmacokinetic characteristics.

V. Toxic Side Effects Experiment

The toxic side effects of the compounds of the present invention (Ia and Ib) were studied. The rats were administered once daily at 30 mg/kg/day for 14 days consecutively. The results showed that the compounds of the present invention had no obvious toxic side effects, and there was no significant difference between the organ tissues, blood biochemical parameters of the rats of the groups of the compounds of the present invention and those of the rat of the vehicle control group. The compounds of the present invention are well tolerated in animals. In the same experiment, under the same dose (30 mg/kg/day) of the similar compound Baricitinib, the thymus and spleen tissues of rats were significantly reduced (a quarter of the normal size) and showed certain toxic side effects.

The above examples are merely representative. As can be seen from the above examples, the compounds of the present invention are ideal JAK kinase inhibitors with high potencies, the compounds can be expected to be used for the treatment or prevention of disease such as rheumatoid arthritis, polycythemia vera, psoriasis, primary thrombocytosis and myelofibrosis and achieve very good results, and they can also be combined with different types of medicinal salts to make oral preparations (tablets or capsules, etc.). Tablets or capsules made with the compounds of the present invention may be taken once or more daily. The compounds of the present invention can also be combined with other drugs to make compound preparations.

The above examples are merely provided to illustrate the technical ideas and features of the present invention, the purposes of the examples are to enable those skilled in the art to understand the contents of the present invention and implement them accordingly, and the protection scope of the present invention is not limited thereto. All equivalent changes or modifications made according to the spirit of the present invention shall fall within the protection scope of the present invention.

The invention claimed is:

1. A pyrrolopyrimidine five-membered azacyclic derivative, a pharmaceutically acceptable salt and hydrate thereof, wherein the structural formula of the derivative is shown in formula (I):

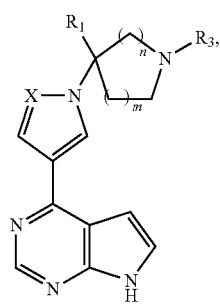
(I)

wherein:

X is N or CH;

$R_1$ is $CH_2CN$ or $COCH_2CN$;

wherein $R_3$ is $SO_2R_4$ or $C(O)R_4$, $R_4$ is a linear or cyclic alkyl group, a linear or branched hydrocarbon chain having at least one double bond, or a linear or cyclic alkyl group substituted with fluorine, $NHCH_3$, $N(CH_3)_2$, phenyl, pyridine or pyrimidine; and m, and n are each an integer of 0-3, and m+n=3.

2. The pyrrolopyrimidine five-membered azacyclic derivative, the pharmaceutically acceptable salt and hydrate thereof according to claim 1, wherein, in the pyrrolopyrimidine five-membered azacyclic derivative, pharmaceutically acceptable salt and hydrate thereof, non-exchangeable hydrogen is not substituted, partially or completely substituted by deuterium.

3. The pyrrolopyrimidine five-membered azacyclic derivative, the pharmaceutically acceptable salt and hydrate thereof according to claim 1, wherein $R_4$ is a linear or cyclic alkyl group having 1 to 6 carbon atoms or a hydrocarbon group having one double bond and having 2 to 6 carbon atoms.

4. The pyrrolopyrimidine five-membered azacyclic derivative, the pharmaceutically acceptable salt and hydrate thereof according to claim 3, wherein $R_4$ is methyl, ethyl, vinyl, or cyclopropyl.

5. The pyrrolopyrimidine five-membered azacyclic derivative, the pharmaceutically acceptable salt and hydrate thereof according to claim 1, wherein, in the formula (I), $R_1$ is $CH_2CN$ and $R_3$ is $SO_2R_4$.

6. The pyrrolopyrimidine five-membered azacyclic derivative, the pharmaceutically acceptable salt and hydrate thereof according to claim 1, wherein, in formula (I), $R_3$ is $SO_2CH_2CH_3$.

7. The pyrrolopyrimidine five-membered azacyclic derivative, the pharmaceutically acceptable salt and hydrate thereof according to claim 1, wherein, the pyrrolopyrimidine five-membered azacyclic derivative is one of the compounds represented by the following structural formulas or a mixture of more thereof:

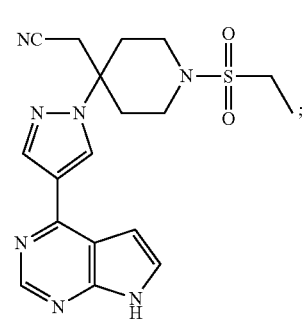
Ia

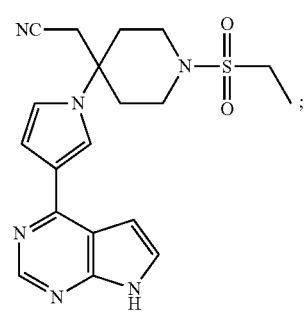
Ib

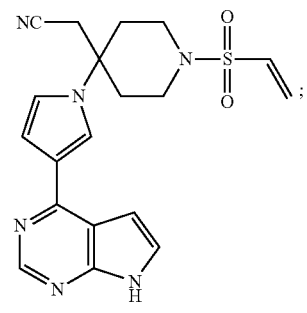
Ic

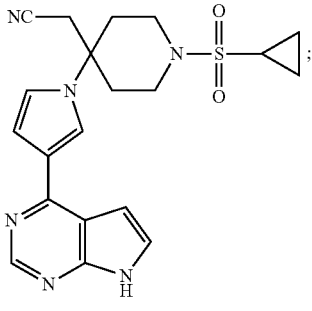
Id

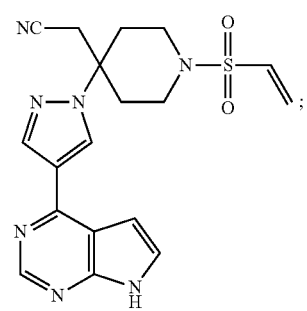
Ie

-continued

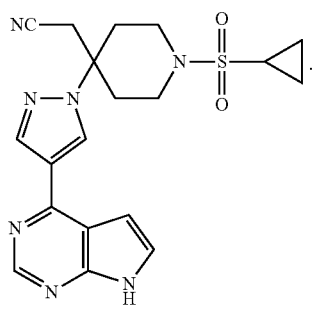

8. A pharmaceutical composition, comprising the pyrrolopyrimidine five-membered azacyclic derivative or the pharmaceutically acceptable salt thereof according to claim 1, and a pharmaceutically acceptable carrier.

9. A method for preventing and/or treating indications related to JAK kinase function in a mammal, comprising administering an effective amount of the pyrrolopyrimidine five-membered azacyclic derivative, the pharmaceutically acceptable salt and hydrate thereof according to claim 1, said indications related to JAK kinase function comprise rheumatoid arthritis, polycythemia vera, psoriasis, primary thrombocytosis and myelofibrosis.

10. A method for preparing the pyrrolopyrimidine five-membered azacyclic derivative according to claim 1, comprising the following steps:

(a) reacting

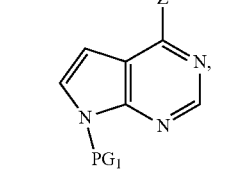

with a first amino protective reagent $PG_1$ to obtain

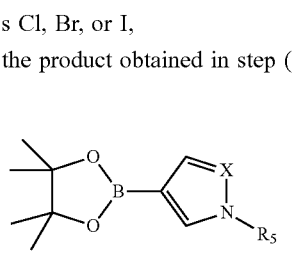

wherein, Z is Cl, Br, or I, (b) reacting the product obtained in step (a) with

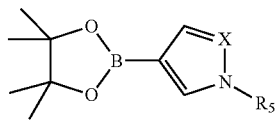

to obtain

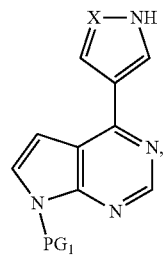

wherein, $R_5$ is an alkoxy group or a silane group which are as amino protecting groups; when $R_5$ being an alkoxy group, first of all, placing the product obtained in step (a) and

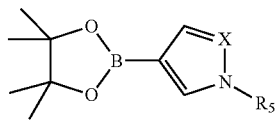

in a mixed solvent of alcohol and water, carrying out the reaction under a palladium catalyst and a basic condition to make the group

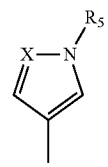

replace Z, and then removing $R_5$ under an acidic reaction condition;

(c) using

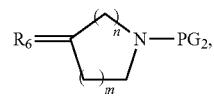

wherein $PG_2$ is a second amino protecting group, and subjecting the product obtained in step (b) to an addition reaction with

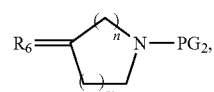

followed by deprotection of the second amino protecting group $PG_2$ under an acidic condition to obtain

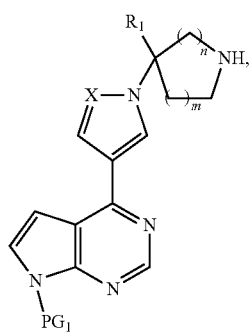

wherein $R_6$ is CHCN or CH(CO)CN, and m, n and $R_1$ are defined as before;

(d) carrying out a substitution reaction in a polar solvent between the product obtained in step (c) and $R_3$—Cl to obtain then removing the first amino protecting group $PG_1$ to obtain

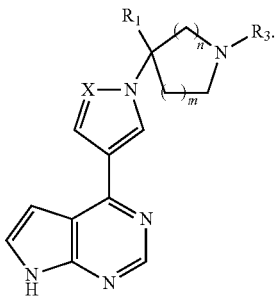

11. The pyrrolopyrimidine five-membered azacyclic derivative, the pharmaceutically acceptable salt and hydrate thereof according to claim 2, wherein, in the formula (I), $R_1$ is $CH_2CN$ and $R_3$ is $SO_2R_4$.

12. The pyrrolopyrimidine five-membered azacyclic derivative, the pharmaceutically acceptable salt and hydrate thereof according to claim 3, wherein, in the formula (I), $R_1$ is $CH_2CN$ and $R_3$ is $SO_2R_4$.

13. The pyrrolopyrimidine five-membered azacyclic derivative, the pharmaceutically acceptable salt and hydrate thereof according to claim 4, wherein, in the formula (I), $R_1$ is $CH_2CN$ and $R_3$ is $SO_2R_4$.

* * * * *